(12) United States Patent
Arinzeh et al.

(10) Patent No.: US 11,617,816 B2
(45) Date of Patent: Apr. 4, 2023

(54) SYSTEM AND METHOD FOR A PIEZOELECTRIC COLLAGEN SCAFFOLD

(71) Applicant: New Jersey Institute of Technology, Newark, NJ (US)

(72) Inventors: Treena Arinzeh, West Orange, NJ (US); Michael Jaffe, Maplewood, NJ (US); Amir Hossein Rajabi, Briarwood, NY (US)

(73) Assignee: New Jersey Institute of Technology, Newark, NJ (US)

( * ) Notice: Subject to any disclaimer, the term of this patent is extended or adjusted under 35 U.S.C. 154(b) by 321 days.

(21) Appl. No.: 16/502,840

(22) Filed: Jul. 3, 2019

(65) Prior Publication Data

US 2020/0009291 A1 Jan. 9, 2020

Related U.S. Application Data

(60) Provisional application No. 62/694,056, filed on Jul. 5, 2018.

(51) Int. Cl.
| | |
|---|---|
| *A61L 27/24* | (2006.01) |
| *D01D 5/00* | (2006.01) |
| *C12M 1/12* | (2006.01) |
| *C12N 5/0775* | (2010.01) |
| *C12N 5/0793* | (2010.01) |
| *D01F 4/00* | (2006.01) |
| *H01L 41/253* | (2013.01) |
| *H01L 41/193* | (2006.01) |
| *C07K 1/00* | (2006.01) |

(52) U.S. Cl.
CPC ............... *A61L 27/24* (2013.01); *C07K 1/00* (2013.01); *C12M 25/14* (2013.01); *C12N 5/0619* (2013.01); *C12N 5/0663* (2013.01); *D01D 5/0007* (2013.01); *D01F 4/00* (2013.01); *H01L 41/193* (2013.01); *H01L 41/253* (2013.01); *A61L 2400/18* (2013.01); *A61L 2430/34* (2013.01); *C12N 2533/54* (2013.01); *C12N 2537/00* (2013.01); *C12N 2537/10* (2013.01); *C12N 2539/00* (2013.01)

(58) Field of Classification Search
CPC .. A61L 27/24; A61L 2430/34; A61L 2400/18; C12M 25/14; C12N 5/0663; C12N 5/0619; C12N 2537/10; C12N 2537/00; C12N 2539/00; C12N 2533/54; D01F 4/00; D01D 5/0007; H01L 41/253; H01L 41/193; H01L 41/257; C07K 1/00
See application file for complete search history.

(56) References Cited

U.S. PATENT DOCUMENTS

| | | |
|---|---|---|
| 9,476,026 B2 | 10/2016 | Arinzeh et al. |
| 2010/0233234 A1 | 9/2010 | Arinzeh et al. |
| 2013/0026088 A1 | 1/2013 | Coster et al. |
| 2014/0333184 A1 | 11/2014 | Wang et al. |
| 2016/0271427 A1 | 9/2016 | Lal |
| 2016/0354515 A1 | 12/2016 | Arinzeh et al. |
| 2018/0103852 A1 | 4/2018 | Dagdeviren et al. |

OTHER PUBLICATIONS

Hartono et al., The 4th International Conference on Theoretical and Applied Physics (ICTAP) 2014, AIP Conf. Proc. 1719, 030021-1-030021-4; doi: 10.1063/1.4943716.*
Khanbareh et al., Smart Materials and Structures, 2014, vol. 23, No. 10, p. 1-11 (Citation H Khanbareh et al. 2014 Smart Mater. Struct. 23 105030).*
Hiratai R, Nakamura M, Yamashita K. Role of collagen and inorganic components in electrical polarizability of bone. J Vet Med Sci. 2014;76(2):205-210. doi:10.1292/jvms.13-0229.*
Ribeiro et al., Colloids and Surfaces B: Bio interfaces, 2015, vol. 136, p. 45-55.*
Rajabi et al., Acta Biomaterialia, 2015, vol. 24, p. 12-23.*
Fukada et al., On the Piezoelectric Effect of Bone, Journal of the Physical Society of Japan, 12:1158-62; 1957.
Bassett, Biologic Significance of Piezoelectricity, Calcified Tissue International, 1:252-72, 1967.
Van den Ende et al., Piezoelectric and Mechanical Properties of Novel Composites of PZT and a Liquid Crystalline Thermosetting Resin, The Journal of Materials Science, 42:6417-6425, 2007.
Minary-Jolandan et al., Nanoscale Characterization of Isolated Individual Type I Collagen Fibrils: Polarization and Piezoelectricity, Nanotechnology, 20:0957-4484, 2009.
Ribeiro et al., Fibronectin Adsorption and Cell Response on Electroactive Poly(vinylidene Fluoride) Films, Biomedical Materials, 1:035004, 2012.
Parssinen et al., Enhancement of Adhesion and Promotion of Osteogenic Differentiation of Human Adipose Stem Cells by Poled Electroactive Poly(vinylidene fluoride), Journal of Biomedical Materials Research Part A, 103:919-28, 2015.
Ducrot, et al., Fabrication of Organic MEMS Resonators, Scientific Reports, 6:19426, 1-7, 2016.
Jana, et al., High Pressure Experimental Studies on CuO: Indication of Re-entrant Multiferroicity at Room Temperature, Scientific Reports, pp. 1-8, 2016.
Yang, et al., Dramatically Improved Piezoelectric Properties of Poly(vinylidene fluoride) Composites by Incorporating Align $TiO_2$@MWCNTs, Composites Science and Technology, 123, 259-267, 2016.
Yu, et al., Bone-Inspired Spatially Specific Piezoelectricity Induces Bone Regeneration, Theranostics, vol. 7, Issue 13, pp. 3387-3397, 2017.
Shepley, et al., Effects of Poling and Crystallinity on the Dielectric Properties of $Pb(In_{frax;1;2}Nb_{frax;1;2})O_3$-$Pb(Mg_{1/3}Nb_{frax;2;3})O_3$-$PbTiO_3$ at Cryogenic Temperatures, Scientific Reports, pp. 1-8, 2019.

(Continued)

*Primary Examiner* — Kade Ariani
(74) *Attorney, Agent, or Firm* — McCarter & English, LLP

(57) ABSTRACT

The present invention provides novel methods for poling piezoelectric materials, e.g., collagen, which are carried out in the absence of liquid media and at a relatively low temperature. The present invention also provides electroactive scaffolds comprising poled collagen for promoting cell growth and differentiation.

15 Claims, 8 Drawing Sheets

(56) References Cited

OTHER PUBLICATIONS

Zhang et al., Ice-Templated Poly(Vinylidene Fluoride) Ferroelectrets, Royal Society of Chemistry, Soft Matter, vol. 15, pp. 825-832, 2019.
U.S. Appl. No. 62/694,056, filed Jul. 5, 2018.

* cited by examiner

A.

B.

A.

B.

A.

B.

A.

B.

C.

US 11,617,816 B2

SYSTEM AND METHOD FOR A PIEZOELECTRIC COLLAGEN SCAFFOLD

RELATED APPLICATIONS

This application claims priority to U.S. Provisional Application No. 62/694,056, filed on Jul. 5, 2018, the entire contents of which are hereby incorporated herein by reference.

FIELD OF THE DISCLOSURE

The present disclosure relates to a piezoelectric material. In particular, the present disclosure relates to inducing piezoelectricity in collagenous scaffolds using polarization for cell growth, attachment, differentiation and/or tissue repair.

BACKGROUND

The general approach to the use of tissue engineering in the repair and/or regeneration of tissue is to combine cells and/or biological factors with a biomaterial that acts as a scaffold for tissue development. The cells should be capable of propagating on the scaffold and acquiring the requisite organization and function in order to produce a properly functioning tissue.

Tissue engineering could involve the use of piezoelectric materials. In particular, piezoelectric materials and native tissues, such as bone, cartilage and tendon, transform mechanical deformation to electric fields, which can result in cellular stimulation (Yasuda, J. *Japanese Orthop. Surg. Soc.* 1954, 28:267-71). The use of piezoelectric biomaterials in tissue engineering scaffolds and medical devices allow for electrical stimulus without external power sources or batteries. The piezoelectricity of bone is attributed to collagen fibrils (Fukada et al., *J. Phys. Soc. Japan* 1957, 12:1158-62; Bassett, Calcified Tissue International 1967, 1:252-72). Recent microscopic advances have verified that the piezoelectricity of collagen fibrils occurs along their longitudinal axis (Minary-Jolandan et al., *Nanotechnology* 2009, 20:0957-4484). Due to the randomness of collagen fiber arrangement in most processed collagenous products, the piezoelectricity of the fibers may be diminished or canceled out. Piezoelectricity perpendicular to the surface of biomaterials has been shown to enhance proliferation and differentiation of cells (Ribeiro et al., Biomedical Materials 2012, 1:035004; Pärssinen et al., J. Biomedical Materials Research Part A 2015, 103:919-28).

Innovative technologies are needed for tissue engineering of inherently complex tissues, in particular, musculo skeletal connective tissue such as articular cartilage and the underlying bone tissue. Accordingly, compositions and methods that are capable of inducing bone and/or cartilage growth and repair are provided herein.

SUMMARY

Described herein are compositions and methods useful for promoting the growth and/or differentiation and/or repair of a cell and/or tissue. In certain aspects, the present invention provides an electroactive, or piezoelectric, biomaterial as an electroactive scaffold for facilitating growth, differentiation, and/or repair of a cell and/or a tissue. Piezoelectric materials act as highly sensitive mechanoelectrical transducers that will generate charges in response to minute vibrational forces. Piezoelectric scaffolds, which demonstrate electrical activity in response to minute mechanical deformation, allow the achievement of local electric fields characteristic of the natural extracellular matrix observed during development and regeneration or repair.

In accordance with an embodiment of the present disclosure, piezoelectricity may be induced, or level of piezoelectricity may be increased, in certain materials by electric poling. As illustrated in FIG. 1, certain materials, such as collagenous materials, may comprise individual dipoles that are oriented randomly, resulting in no piezoelectricity, or low piezoelectricity of the material. During poling, strong electric field is applied to the material, causing the individual dipoles to align in the electric field, which results in increased piezoelectricity of the material. As illustrated in FIG. 1, piezoelectricity may be induced perpendicular to the surface of collagenous material. Inducing piezoelectricity in processed collagen is of benefit because collagen is nontoxic and biodegradable. In addition, piezoelectricity may be induced not only in collagen but also in collagen derived materials, such as gelatin, and other proteins for grafts, scaffolds, implants and biomedical devices, by electric poling. Electric poling alters the polarity and piezoelectric coefficient in these materials and can result in a beneficial cellular response.

Accordingly, in some embodiments, the present invention provides a method of poling piezoelectric material that comprises exposing the piezoelectric material to a constant electric field; wherein said method is carried out at a temperature of about 80° C. or less. In some aspects, the method is carried out in the absence of a liquid medium.

In some embodiments, the method is carried out at a temperature of about 25° C. to about 80° C., e.g., about 50° C.

In some embodiments, the method comprises exposing the piezoelectric material to a constant electric field of about $0.5 \times 10^6$ to about $10^7$ V/m, e.g., about $4.4 \times 10^6$ V/m. In some embodiments, the method comprises applying to the piezoelectric material an electric voltage of about 1 kV to about 50 kV.

In some aspects, the piezoelectric material is sandwiched between Teflon and steel plates during exposure to the constant electric field.

In some aspects, the piezoelectric material comprises a polymer, e.g., a naturally derived polymer. The polymer may be biocompatible, biodegradable or both.

In some embodiments, the polymer is selected from the group consisting of collagen, gelatin, zein, elastin, silk, chitosan, chitin, alginate, starch, cellulose, proteoglycans and a glycosaminoglycan. In one aspect, the polymer is collagen. In another aspect, the polymer is gelatin.

In some aspects, the polymer is in a form of a fiber, e.g., an electro spun fiber.

In some embodiments, the present invention also provides an electroactive scaffold for growing and differentiating a differentiable cell comprising the piezoelectric material poled according to the methods of the present invention. In one aspect, the piezoelectric material may comprise a polymer, e.g., collagen.

In some aspects, the electroactive scaffold of the present invention may comprise a polymer in the form of an electro spun collagen fiber.

In some embodiments, the present invention also provides a method of promoting growth or differentiation of a differentiable cell comprising seeding said cell on the electroactive scaffold of the invention.

In some aspects, the present invention also provides a method of promoting tissue repair comprising administering to a subject in need thereof the electroactive scaffold of the invention.

Any combination and/or permutation of the embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

To assist those of skill in the art in making and using the disclosed collagenous scaffold and associated systems and methods, reference is made to the accompanying figures, wherein:

FIG. 3, Panel B is a bar graph illustrating distribution of diameters of electro spun collagen fibers prior to crosslinking.

DETAILED DESCRIPTION

Figure 1:
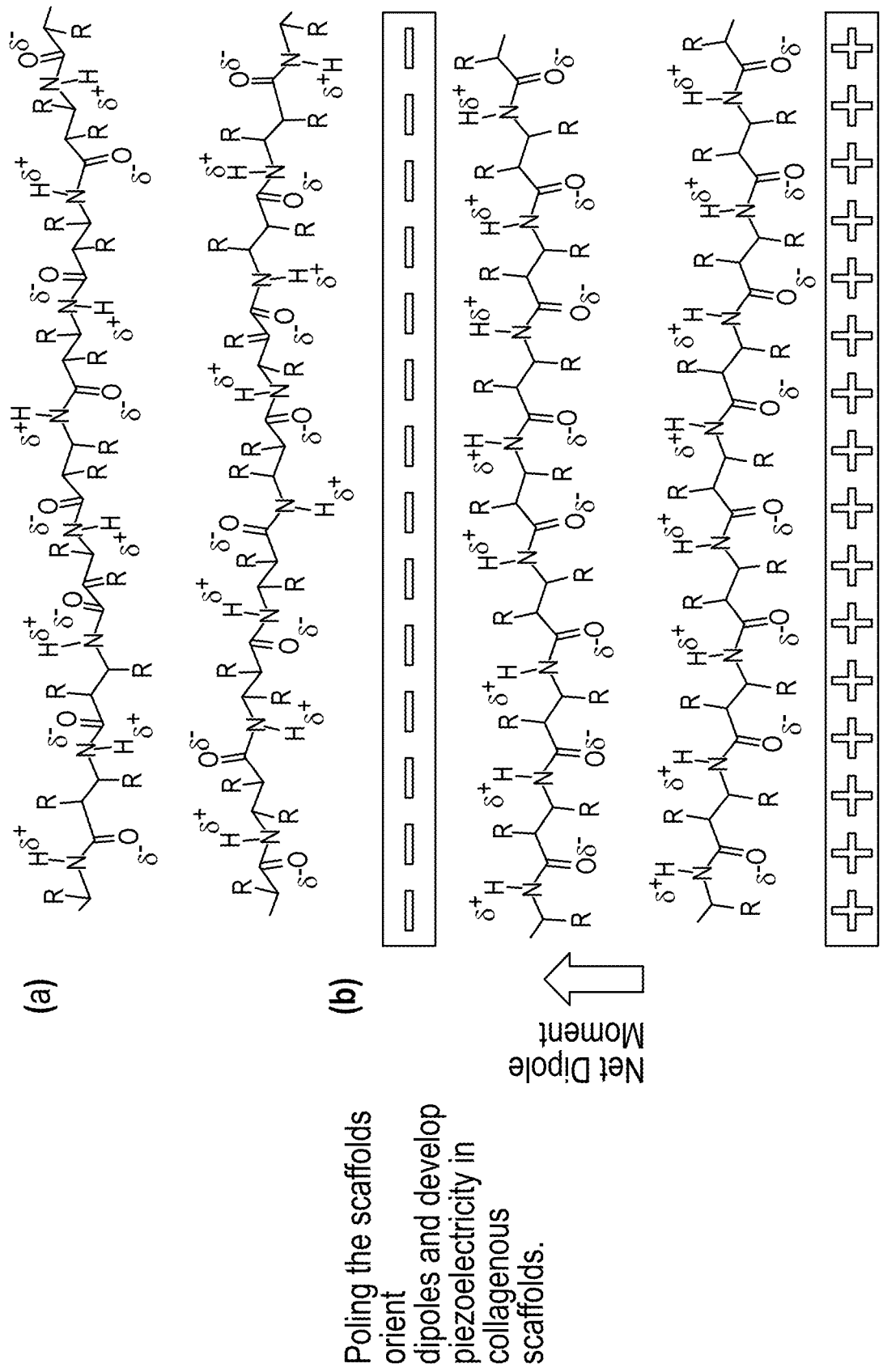
FIG. 1 is a schematic illustrating the effect of poling on the structure of collagenous scaffolds.

The materials and the methods of the present disclosure used in one embodiment will be described below. While this embodiment discusses the use of specific compounds and materials, it is understood that the method could be employed using similar materials. Similar quantities or measurements may be substituted without altering the method embodied below.

The present invention provides a method of poling piezoelectric material. The method of poling of piezoelectric material provided by the present invention is advantageous because, in some embodiments, it avoids the use of a liquid medium, such as silicon oil, which may cause contamination when working with natural materials. Instead, in some embodiments, the method of poling provided by the present invention is carried out in air.

Accordingly, in some embodiments, the present invention provides a method of poling piezoelectric material that comprises exposing the piezoelectric material to a constant electric field, wherein the method is carried out in the absence of a liquid medium. In some embodiment, the method of poling of the present invention does not involve a risk, or is associated with a reduced risk, of contamination of the piezoelectric material typically associated with the use of a liquid medium, e.g., silicon oil.

Another advantage provided by the method of poling piezoelectric material of the present invention involves the use of temperatures that are lower than temperatures which are typically used for poling. For example, the method of poling piezoelectric material of the present invention may be carried out at temperatures of about 80° C. or lower, e.g., at about 50° C. In comparison, methods for poling piezoelectric material known in the art may use higher temperatures, e.g., of at least about 85° C. or about 100° C. (see, e.g., US Patent Publication No. 2013/0026088), about 130° C. (see, e.g., US Patent Publication No. 2016/0271427), or about 150° C. (see, e.g., US Patent Publication No. 2018/0103852), or about 200° C. (see, e.g., van den Ende et al., *J. Mater. Sci.* 2007, 42:6417-25). The use of lower temperatures during poling allows to avoid degradation of the piezoelectric material, e.g., naturally derived polymeric material, such as collagen.

Accordingly, in some embodiments, the present invention provides a method of poling piezoelectric material that comprises exposing the piezoelectric material to a constant electric field; wherein the method is carried out at a temperature of about 80° C. or less. For example, in some embodiments, the method of poling provided by the present invention may be carried out at a temperature of about 25° C. to about 80° C., e.g., about 25° C. to about 55° C., about 30° C. to about 65° C., about 40° C. to about 60° C., about 45° C. to about 55° C., or at about 50° C.

In some embodiments, the method of poling piezoelectric material provided by the present invention may involve exposing the piezoelectric material to a constant electric field. In some embodiments, the electric field may be a high electric field, e.g., of about $0.5 \times 10^6$ to about $10^7$ V/m, e.g., about $0.5 \times 10^6$ V/m to about $8 \times 10^6$ V/m, about $2 \times 10^6$ V/m to about $6 \times 10^6$ V/m, about $3.5 \times 10^6$ V/m to about $5 \times 10^6$ V/m, or about $4.4 \times 10^6$ V/m.

In some embodiments, the method of poling piezoelectric material provided by the present invention may involve applying to the piezoelectric material an electric voltage. In some embodiments, the electric voltage may be a high electric voltage, e.g., of about 1 kV to about 50 kV, e.g., about 1 kV to about 30 kV, about 5 kV to about 20 kV, about 10 kV to about 15 kV, about 10 kV or about 15 kV.

In some embodiments, exposing of the piezoelectric material to a constant electric field may be carried out for at least about 15 minutes, e.g., about 15 minutes to about 5 hours, about 30 minutes to about 4 hours, about 45 minutes to about 2 hours, or for about 1 hour.

Figure 2:
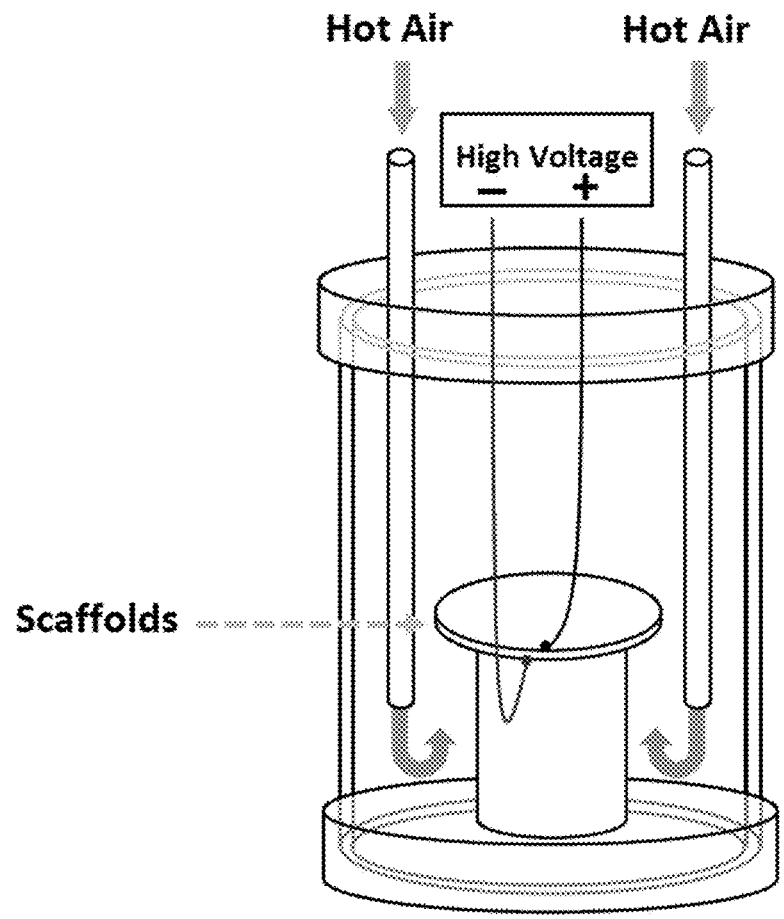
FIG. 2 is a schematic illustrating the electric poling setup in accordance with an embodiment of the present invention.

In some embodiments, the method of poling of a piezoelectric material may involve placing the piezoelectric material in a chamber, sandwiched between two plates, e.g., a Teflon plate and a steel plate, to create a sandwich of a known thickness. The elevated temperature, e.g., of about 80° C. or less, such as about 50° C., may be maintained in the chamber by purging hot air inside the chamber until the desired temperature is reached. After poling, to maintain the orientation of the dipoles, the chamber may be cooled down to a desired temperature, e.g., room temperature, by purging cold air inside the chamber. An exemplary chamber that may be used to carry out the method of poling of the present invention is illustrated in FIG. 2. An exemplary procedure describing poling of piezoelectric material in accordance with methods of the present invention is described in Example 2 and Example 4.

In some examples, method of poling of piezoelectric material of the present invention may be used to produce negatively poled piezoelectric material. This may be accomplished by, e.g., connecting one the plates of the sandwich, e.g., top steel plate, to a positive voltage, while grounding the bottom plate.

In other examples, a method of poling of piezoelectric material of the present invention may be used to produce positively poled piezoelectric material. This may be accomplished by, e.g., connecting one the plates of the sandwich, e.g., top steel plate, to a negative voltage, while grounding the bottom plate.

In some embodiments, the positively poled piezoelectric material and the negatively poled piezoelectric material may produce different biological effects. For example, as illustrated in Example 3, negatively poled collagenous scaffolds were shown to promote growth of hMSCs, while positively poled collagenous scaffolds were shown to promote osteogenic differentiation of hMSCs.

In some embodiments, the piezoelectric material that may be poled in accordance with methods of the present invention may comprise a polymer, e.g., a naturally derived polymer. The polymer, e.g., the naturally derived polymer may be biocompatible, biodegradable, or both. For example, the piezoelectric material may comprise a polymer selected from the group consisting of collagen, gelatin, zein, elastin, silk, chitosan, chitin, alginate, starch, cellulose, proteoglycans and a glycosaminoglycan. In one embodiment, the polymer is collagen. In another embodiment, the polymer is gelatin.

In some embodiments, the piezoelectric material may comprise a polymer which is in a form a fiber, e.g., an electrospun fiber. Electrospinning is useful for fabricating tissue engineering scaffolds and is carried out by applying a high voltage to a polymeric solution. The basic principle behind this process is that an electric voltage sufficient to overcome the surface tension of a solution causes the droplets to elongate so that the polymer, e.g., collagen, is splayed randomly as very fine fibers, which when collected on a plate, form a non-woven mat or mesh. Traditionally, electrospinning has yielded non-woven (i.e., mesh) mats (also called matrices and scaffolds) of nanometer sized fiber diameters and nanometer sized pore diameters. However, in order for cells to infiltrate into a scaffold and proliferate, micron sized fiber diameters and micron sized pore diameters are optimal. Because the diameter of a cell is approximately about 10 µm to about 20 µm, pores of this size or greater are optimal for allowing for cell infiltration. Thus, in some embodiments, the piezoelectric material comprises a non-woven mesh of electrospun fibers of a polymer, such as collagen. In one specific example, the piezoelectric material is a collagenous scaffold formed by electrospinning a solution of collagen to produce a scaffold, e.g., a non-woven mesh.

In some embodiments, the piezoelectric material that may be poled in accordance with methods of the present invention may comprise a scaffold, e.g., a scaffold that may be useful for cell attachment, proliferation and/or differentiation. In one example, the scaffold may be a fibrous scaffold, i.e., comprising polymeric fibers. The scaffold may also be a film or a coating, e.g., polymeric coating. In one example, the piezoelectric material may comprise a fibrous scaffold, e.g., a scaffold of collagenous fibers. In one specific embodiment, the piezoelectric material is a non-woven mesh comprising electrospun fibers, such as electrospun collagen fibers. In other examples, the piezoelectric material may comprise a coating, e.g., a polymeric coating, which may be present, for example, on a cell culture plate.

Methods of poling piezoelectric material provided by the present invention allow, for the first time, preparation of electroactive scaffolds comprising naturally derived polymers, e.g., collagen, for tissue engineering. It is known that electroactive materials promote cell growth and differentiation (see., e.g., US Patent Publication No. 2016/0354515 A1, the entire contents of which are hereby incorporated herein by reference), however, electroactive scaffolds comprising electrospun fibers of naturally derived polymers, such as collagen, could not be produced prior to the present invention. Electroactive scaffolds comprising naturally derived polymers are advantageous over scaffolds comprising conventional piezoelectric materials, such as piezoelectric ceramics or synthetic piezoelectric polymers, which are often immunogenic or non-biodegradable and may not be well-tolerated in the body. Naturally derived polymers, such as collagen, are both biocompatible and biodegradable, and mimic the piezoelectric behavior of natural tissues such as bone and cartilage. When used as an implant for tissue regeneration, a piezoelectric scaffold comprising a naturally derived polymer, such as collagen, will degrade in vivo, leaving behind regenerated tissue.

Accordingly, in some embodiments, the present invention also provides an electroactive scaffold comprising a poled polymer, e.g., a poled naturally derived polymer. In one specific embodiment, the naturally derived polymer may be selected from the group consisting of collagen, gelatin, zein, elastin, silk, chitosan, chitin, alginate, starch, cellulose, proteoglycans and a glycosaminoglycan. In one example, the naturally derived polymer is collagen. In another example, the naturally derived polymer is gelatin. In some embodiments, the electroactive scaffold comprises fibers, e.g., electrospun fibers. In one specific example, the electroactive scaffold comprises a non-woven mesh of electrospun fibers of a polymer, such as collagen. In some embodiments, the electroactive scaffold has been prepared by poling piezoelectric material comprised in the scaffold in accordance with methods of the present invention.

In some examples, the polymer, e.g., naturally derived polymer, comprised in an electroactive scaffold of the present invention is positively poled. In other examples, the polymer, e.g., naturally derived polymer comprised in an electroactive scaffold of the present invention is negatively poled.

In some examples, an electroactive scaffold provided by the present invention further comprises a cell. The cell may be a stem cell, e.g., a mesenchymal stem cell (MSC) or a neural cell, e.g., a primary neuron. In some embodiments, the cell may be derived from a donor, e.g., a subject to be administered the electroactive scaffold in accordance with methods of the present invention. For example, the cell may be isolated from a donor and cultured in the presence of an electroactive scaffold of the present invention. In some examples, the electroactive scaffold of the present invention comprises a non-woven mesh of electrospun fibers, e.g., electrospun collagen fibers, and a cell, e.g., an MSC or a neural cell, that is attached to the electrospun fibers.

In some embodiments, the present invention also provides a method of promoting growth or differentiation of a differentiable cell comprising seeding the cell on the electroactive scaffold of the invention. One the electroactive scaffold is seeded with cells, it may be incubated with cell culture media to promote cell growth and differentiation. The cell may be a stem cell, e.g., a mesenchymal stem cell (MSC). The cell may also be a neural cell, e.g., a primary neuron.

In some embodiments, the present invention also provides a method of promoting tissue repair comprising administering to a subject in need thereof the electroactive scaffold as described herein, such as a scaffold comprising a poled polymer, e.g., a naturally derived polymer. In one embodiment, the poled naturally derived polymer is poled collagen.

In some examples, the electroactive scaffold to be administered to a subject may comprise a cell, e.g., a stem cell, such as an MSC, or a neural cell, such as a primary neuron. In some embodiments, the cell may be derived from a donor, e.g., a subject to be administered the electroactive scaffold in accordance with methods of the present invention. For example, the cell may be isolated from a donor and cultured in the presence of an electroactive scaffold of the present invention before the electroactive scaffold is administered to a subject. In some examples, the electroactive scaffold to be administered to a subject invention may comprise a non-woven mesh of electrospun fibers, e.g., electrospun collagen fibers, and a cell, e.g., an MSC or a neural cell, that is attached to the electrospun fibers. The electroactive scaffold used for promoting tissue repair in accordance with methods of the present invention may be a part of an implant or graft for administering to a subject.

EXAMPLES

Example 1. Preparation of Collagenous Scaffolds

Figure 3:
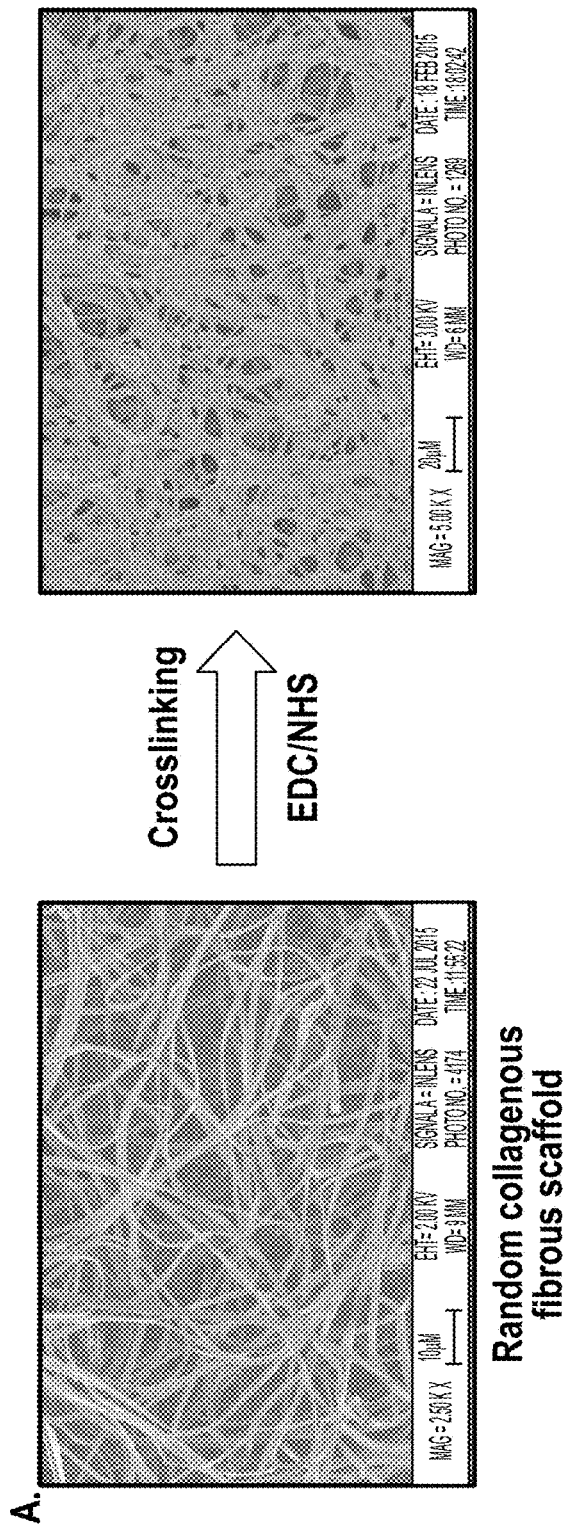
FIG. 3, Panel A is a series of confocal microscopic images of collagenous scaffold before and after crosslinking.

Collagen from bovine dermis was dissolved in mixtures of concentrated phosphate-buffered saline and ethanol and subsequently electrospun to form electrospun fibers in a non-woven mesh. The diameters of the electrospun fibers were measured. Subsequently, the electrospun mats were post-crosslinked in a mixture of 200 mM of 1-Ethyl-3-(3-dimethylaminopropyl) carbodiimide.HCl (EDC, Novabiochem®) and 40 mM of N-hydroxysuccinimide (NHS, Sigma-Aldrich) in anhydrous ethanol for 96 hours. The resulting crosslinked collagenous scaffolds comprise a non-woven mesh of random and/or aligned nanofibers or microfibers, or a combination of both. The electrospun scaffolds before and after crosslinking are shown in FIG. 3, Panel A. The bar graph illustrating fiber diameter distribution is shown in FIG. 3, Panel B and indicates that the collagenous electrospun fibers have a diameter of between about 1.5 µm and about 5 µm.

Example 2. Poling of Collagenous Scaffolds

The crosslinked scaffolds prepared in Example 1 were vacuum dried and sandwiched between parallel circular Teflon and steel plates. The sandwiched scaffolds were then placed in a chamber as demonstrated in FIG. 2.

To electrically pole the scaffolds, a constant electric field of $4.4 \times 10^6$ V/m was reached by applying an electric voltage of 10 kV across the sandwich with a known thickness. After applying the electric field, the temperature of the scaffolds was increased by purging hot air inside the chamber. After the maximum temperature of approximately 50° C. was reached, the hot air purge was adjusted to maintain the temperature and the electric field constant for 1 hour. To maintain the orientation of the dipoles, the chamber was cooled down to room temperature by purging cold air, while the electric field was kept constant at $4.4 \times 10^6$ V/m. After the chamber reached room temperature, the voltage was released, and the scaffolds were removed. This method was used to produce both positively and negatively poled collagenous scaffolds. The surface of the scaffold in contact with the positive electrode is the negatively charged surface and the opposite surface of the scaffold, in contact with the negative electrode, is the positively charged surface. Dipoles are oriented in the direction of the applied field.

After electric poling, all scaffolds were rehydrated and punched with 6 mm and 10 mm diameter biopsy punches, for 96-well plates and 24-well plates, respectively. The punched scaffolds were then sterilized in 100% ethanol for 20 minutes and placed in low attachment polypropylene plates (Fisher Scientific).

To compare the piezoelectricity of the unpoled and electrically poled collagen scaffolds, pressure sensors were fabricated by sandwiching non-crosslinked electrospun collagen before and after electric poling between copper ribbons. The pressure sensors were compressed sinusoidally by a texture analyzer (TA-XT2) in the direction of poling. The signals generated by the sensor were collected by an oscilloscope (Tektronix DPO4000B). This technique was adopted from the dissertation of Sita Damaraju (Damaraju S M, "Piezoelectric Scaffolds for Osteochondral Defect Repair: New Jersey Institute of Technology; 2015).

Figure 4:
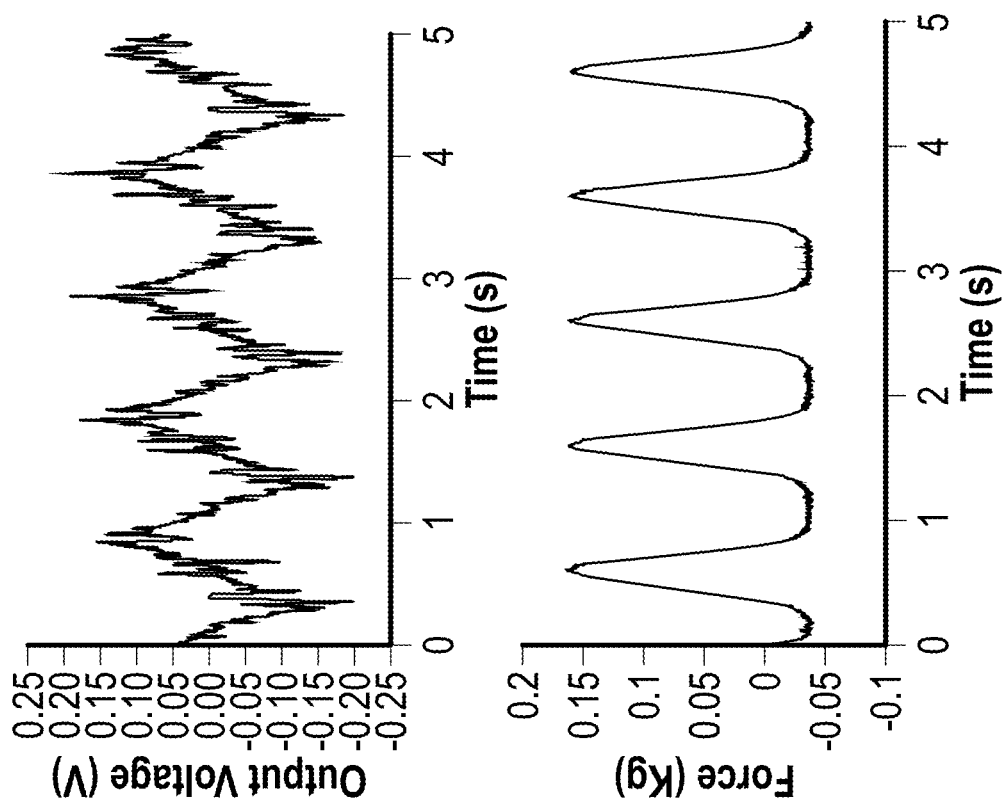
FIG. 4 is a series of graphs illustrating signals resulting from deforming unpoled (Panel A) and poled (Panel B) collagenous scaffolds.
Figure 4:
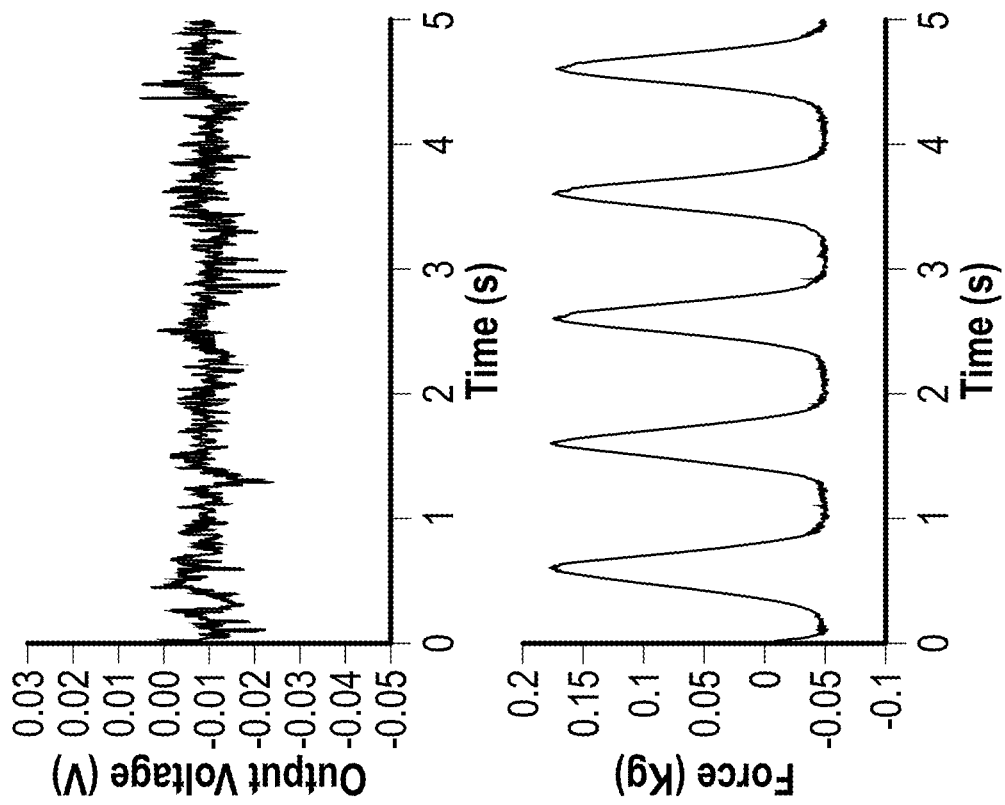

The signals generated by the sensor for the unpoled and poled collagenous scaffolds are shown in FIG. 4. As illustrated in FIG. 4, Panel A, there were no effective signals resulting from deforming unpoled collagenous scaffolds. As illustrated in FIG. 4, Panel B, in-phase electric signal emitted from poled collagenous scaffolds as a result of deformation. The signal to noise ratio was high, suggesting that the electrically poled electrospun collagen demonstrates piezoelectric response normal to the surface of the scaffold.

Example 3. Growth and Differentiation of hMSCs on Poled Collagenous Scaffolds

Human bone marrow-derived mesenchymal stem cells (hMSC, Lonza Biosciences, USA) were expanded and seeded at $2.1 \times 10^4$ cells/cm$^2$ and $3.8 \times 10^4$ cells/cm$^2$ on unpoled, positively poled and negatively poled scaffolds in 96- and 24-well polypropylene plates, respectively. As controls, same number of cells were seeded on 96 and 24 well tissue culture polystyrene plates (TCP). The media of half of the groups were changed with osteogenic media after 24 hours, and called osteogenic samples, while the rest were changed with fresh general media and called general samples. The media of all groups were changed every 48 hours. Cells were harvested at the day of the first media change (considered as day 0) as well as 4, 7, 14 and 21 days for cellular proliferation by PicoGreen assay, alkaline phosphatase activity and calcium mineralization measurements. Cells were imaged by confocal fluorescent microscope (C1-si, Nikon) after staining F-actin and the nuclei.

Figure 5:
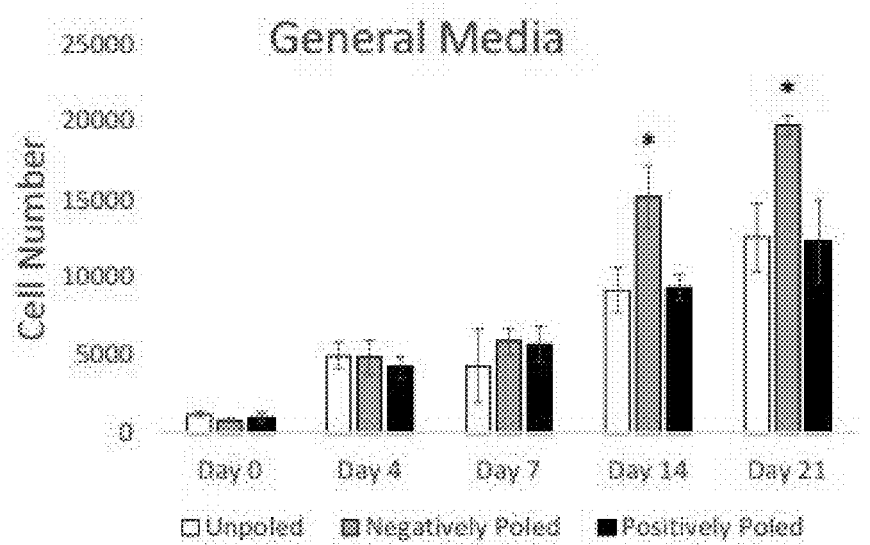
FIG. 5 is a series of bar graphs showing cell numbers on the unpoled, negatively poled and positively poled collagen scaffolds in general media (Panel A) and osteogenic media (Panel B). In the bar graphs, * is p<0.05 between negatively poled collagen fibers and positively poled collagen fibers, as well as between negatively poled collagen fibers and unpoled collagen fibers. Values are Mean+Standard Error.
Figure 5:
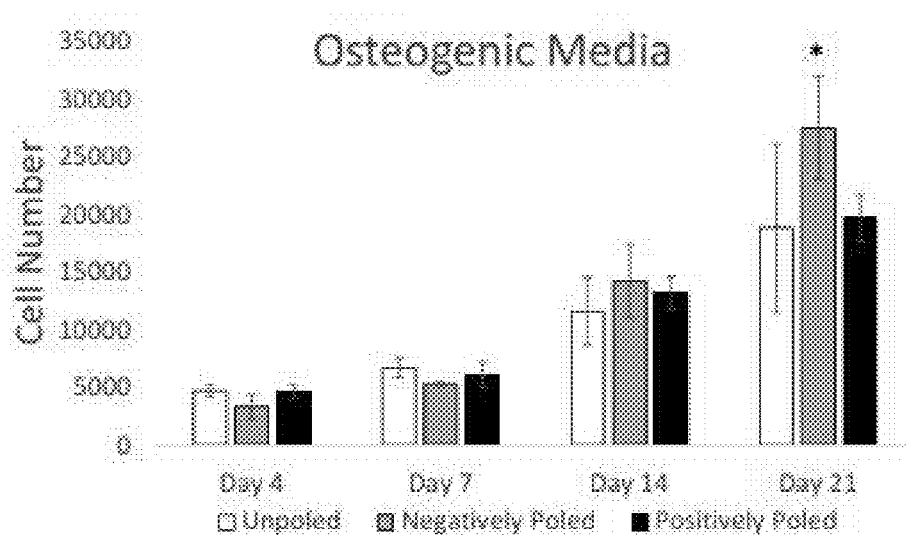

FIG. 5 is a series of bar graphs showing cell numbers on the unpoled, negatively poled and positively poled collagen scaffolds in general media (Panel A) and osteogenic media (Panel B). In the bar graphs, * is p<0.05 between negatively poled collagen fibers and positively poled collagen fibers, as well as between negatively poled collagen fibers and unpoled collagen fibers. Values are Mean±Standard Error. As is evident from FIG. 5, at days 14 and 21, the mesenchymal stem cells on the negatively-poled scaffolds in general and osteogenic media showed significantly higher proliferation than on the unpoled and positively-poled scaffolds.

Figure 6:
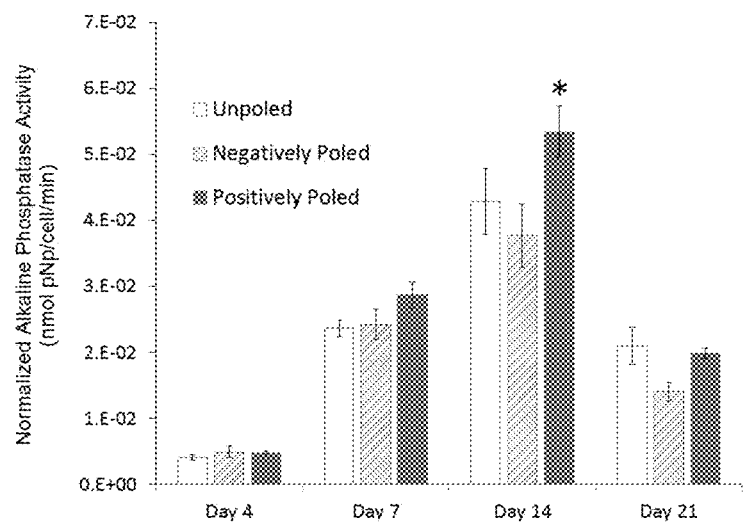
FIG. 6 is a series of bar graphs showing alkaline phosphatase activity (Panel A) and calcium mineralization (Panel B), both of which are indicative of osteogenic differentiation. In panel A, * is p<0.05 between positively poled collagen fibers and the negatively poled collagen fibers at day 14, with values being Mean±Standard Error. In panel B, * is p<0.05 between positively poled and unpoled collagen fibers at day 14, ** is p<0.05 between positively poled and negatively poled collagen at day 14. Values are Mean±Standard Error.
Figure 6:
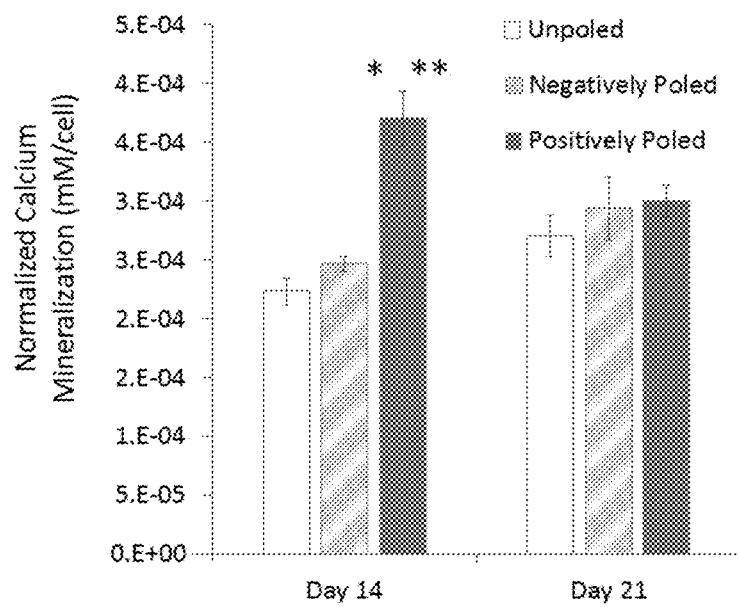

FIG. 6 is a series of bar graphs showing alkaline phosphatase activity (Panel A) and calcium mineralization (Panel B), both of which are indicative of osteogenic differentiation. In Panel A, * is p<0.05 between positively poled collagen fibers and the negatively poled collagen fibers at day 14, with values being Mean±Standard Error. In panel B, * is p<0.05 between positively poled and unpoled collagen fibers at day 14, ** is p<0.05 between positively poled and negatively poled collagen at day 14. Values are Mean±Standard Error. As can be seen from FIG. 6, Panel A and FIG. 6, Panel B, positively poled collagenous scaffolds promoted the osteogenic differentiation of mesenchymal stem cells.

Figure 7:
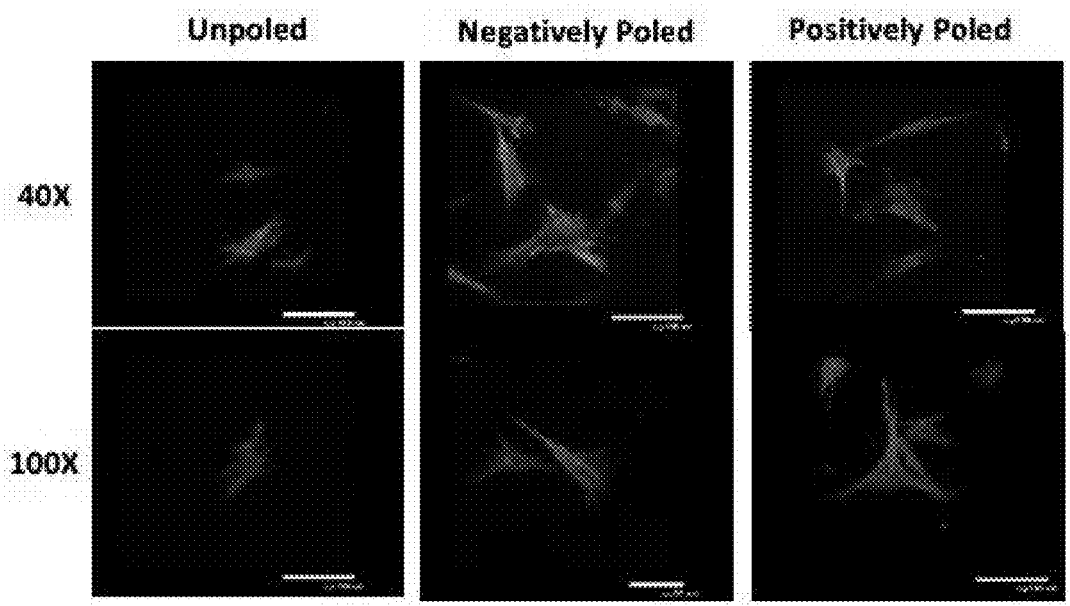
FIG. 7 is a series of confocal microscopic images of hMSCs in unpoled, negatively-poled and positively-poled electrospun collagenous scaffolds. Panel A shows hMSCs 24 hours after seeding in general media, while Panel B shows hMSCs 4 days after seeding in general and osteogenic media.
Figure 7:
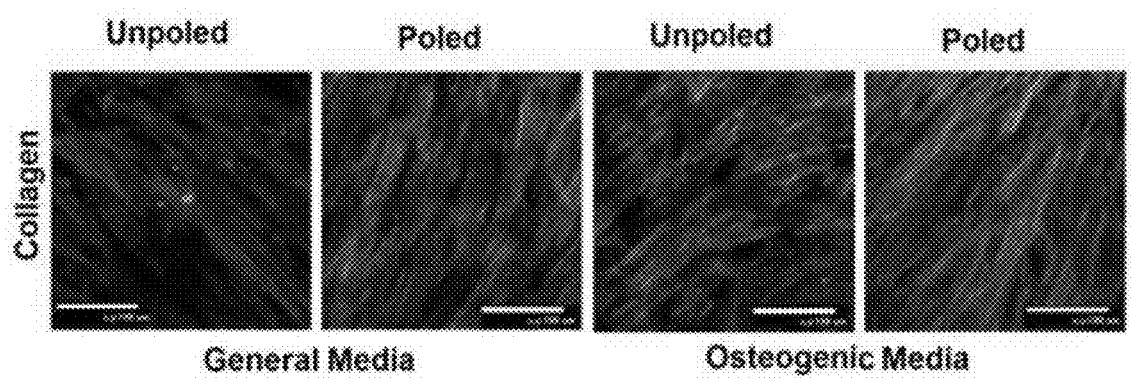

FIG. 7 is a series of confocal microscopic images of hMSCs in unpoled, negatively-poled and positively-poled electrospun collagenous scaffolds. Panel A shows hMSCs 24 hours after seeding in general media, while Panel B shows hMSCs 4 days after seeding in general and osteogenic media. FIG. 7 indicates that cells on poled collagenous scaffolds were more spread with more pronounced actin filaments than on unpoled collagen.

Example 4. Attachment and Growth of Primary Neurons on Poled Collagenous Scaffolds The goal of this experiment was to determine the effect of poling of collagenous scaffolds the attachment and outgrowth of primary neurons. For this experiment, poling of collagenous scaffolds was carried out after the punched scaffolds were sterilized and dried inside 24-well polypropylene plates. While one of the polypropylene plates was labeled as unpoled and stayed untreated, the other two plates were sealed and sandwiched between circular steel plates in the chamber as shown in FIG. 2. For negative poling, the top steel plate was connected to a positive voltage of 15 kV, while the bottom plate was grounded. For positive poling, the top steel plate was connected to a negative voltage, while the bottom plate was grounded. The positively poled and negatively poled groups were poled in opposite directions. The temperature was increased to approximately 50° C. and maintained for 1 hour, while the voltage remained constant. The scaffolds were then poled for 1 hour at the maximum temperature of approximately 50° C. After 1 hour, the voltage was kept constant, but cool air was purged until the chamber reached room temperature in order to freeze the oriented dipoles.

Single dorsal root ganglia (DRGs) were isolated from E17 rat embryos. The isolated DRGs were then seeded with 10 μl of the medium on the unpoled, negatively poled and positively poled collagenous scaffolds. After one hour of incubation, 300 μl of the medium was added to every well. The media in all wells was changed after 48 hours. After 4 days, the DRGs were fixed with 4% formaldehyde (PFA) in phosphate-buffered saline (PBS) and stained red for neurofilaments. The DRGs were then imaged by confocal fluorescent microscope (C1-si, Nikon).

Figure 8:
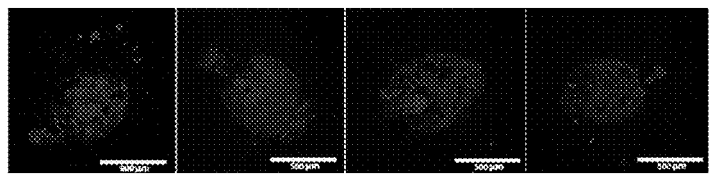
FIG. 8 shows confocal images of four DRGs after 4 days on the unpoled collagenous scaffolds (Panel A), negatively poled scaffolds (Panel B) and positively poled scaffolds (Panel C). In all images, magnification is 10× and the scale bar is 500 μm.
Figure 8:
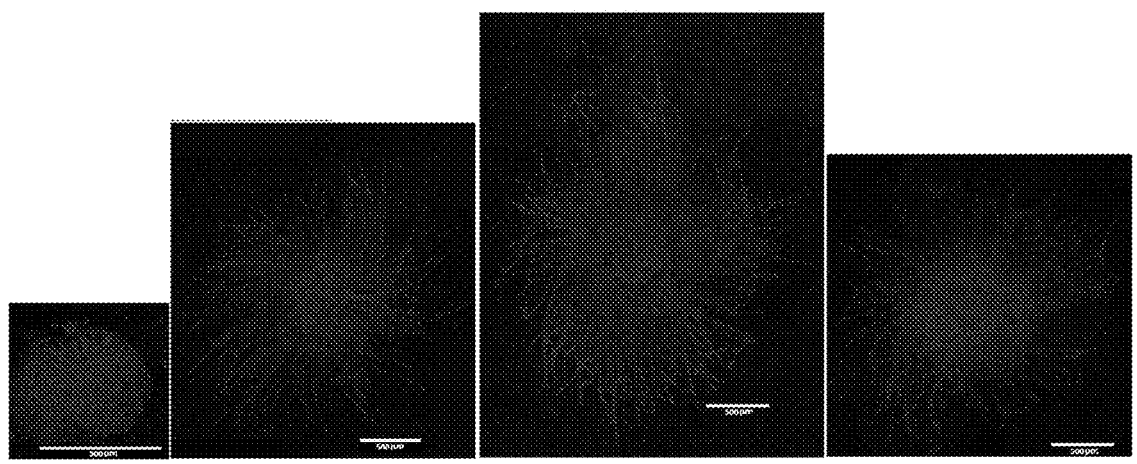
Figure 8:
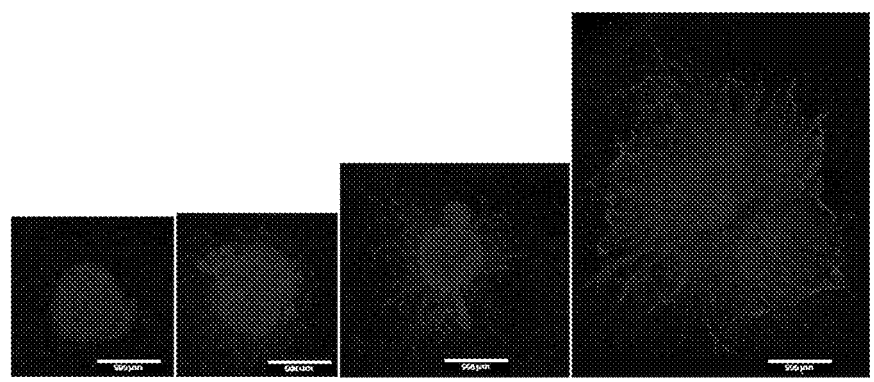

FIG. 8 shows confocal images of four DRGs after 4 days on the unpoled collagenous scaffolds (Panel A), negatively poled scaffolds (Panel B) and positively poled scaffolds (Panel C). In all images, magnification is 10× and the scale bar is 500 μm. FIG. 8 indicates that the poled scaffolds promoted the attachment and outgrowth of the primary neurons. Three of the four DRGs on the negatively-poled scaffolds exhibited pronounced and stretched axons, as shown in FIG. 8, Panel B, while none of the DRGs expanded on the unpoled scaffolds, as shown in FIG. 8, Panel A. Half of the DRGs on the positively poled scaffolds showed attachment, and only one of them expanded well on the scaffold, as shown in FIG. 8, Panel C.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

What is claimed is:

1. A method of preparing a scaffold comprising poled piezoelectric material, said method comprising exposing a scaffold comprising piezoelectric material to a constant electric field;
   wherein said method is carried out at a temperature of about 80° C. or less;
   wherein said piezoelectric material is a naturally derived polymer; and
   wherein said scaffold is a fibrous scaffold, thereby preparing the scaffold comprising poled piezoelectric material.

2. The method of claim 1, wherein said method is carried out in the absence of a liquid medium.

3. The method of claim 1, wherein said method is carried out at a temperature of about 25° C. to about 80° C.

4. The method of claim 3, wherein said method is carried out at a temperature of about 50° C.

5. The method of claim 1, wherein said method comprises exposing said piezoelectric material to a constant electric field of about $0.5 \times 10^6$ to about $10^7$ V/m.

6. The method of claim 1, wherein said method comprises exposing said piezoelectric material to a constant electric field of about $4.4 \times 10^6$ V/m.

7. The method of claim 1, wherein said method comprises applying to the piezoelectric material an electric voltage of about 1 kV to about 50 kV.

8. The method of claim 1, wherein the piezoelectric material is sandwiched between polytetrafluoroethylene and steel plates during exposure to the constant electric field.

9. The method of claim 1, wherein said polymer is biocompatible, biodegradable or both.

10. The method of claim 1, wherein said polymer is selected from the group consisting of collagen, gelatin, zein, elastin, silk, chitosan, chitin, alginate, starch, cellulose, a proteoglycan and a glycosaminoglycan.

11. The method of claim 10, wherein said polymer is collagen.

12. The method of claim 1, wherein said fibrous scaffold further comprises a mesh of electrospun fibers.

13. The method of claim 1, wherein the scaffold comprising poled piezoelectric material emits in-phase electric signals as a result of deformation.

14. The method of claim 1, wherein the piezoelectric material is negatively poled.

15. The method of claim 1, wherein the piezoelectric material is positively poled.

\* \* \* \* \*